United States Patent [19]
Browne

[11] 4,216,791
[45] Aug. 12, 1980

[54] REFLUX CHECK VALVE

[76] Inventor: Ronald O. Browne, 2420 Calle Galicia, Santa Barbara, Calif. 93109

[21] Appl. No.: 873,552

[22] Filed: Jan. 30, 1978

[51] Int. Cl.² .............................................. F16K 17/00
[52] U.S. Cl. ..................................... 137/199; 137/613
[58] Field of Search ........................ 137/197, 199, 613

[56] References Cited

U.S. PATENT DOCUMENTS

| | | | |
|---|---|---|---|
| 2,601,216 | 6/1952 | White | 137/197 UX |
| 2,713,871 | 7/1955 | Kroder | 137/197 |
| 2,734,521 | 2/1956 | Hencken | 137/197 |

FOREIGN PATENT DOCUMENTS 171642  6/1960  Sweden ..................................... 137/199

*Primary Examiner*—Alan Cohan
*Attorney, Agent, or Firm*—Donald D. Mon

[57] ABSTRACT

A check valve is inserted in a tubing such as a catheter for transmission of dry gas such as to the bladder of a person. It prevents the flow of liquid such as urine through it by means of a plug of a foam material which permits the flow of dry gas through it and past end discs of a material which expands in the presence of liquid to plug up the passageway of the valve thereby preventing liquid from flowing through it.

5 Claims, 6 Drawing Figures

U.S. Patent   Aug. 12, 1980   4,216,791
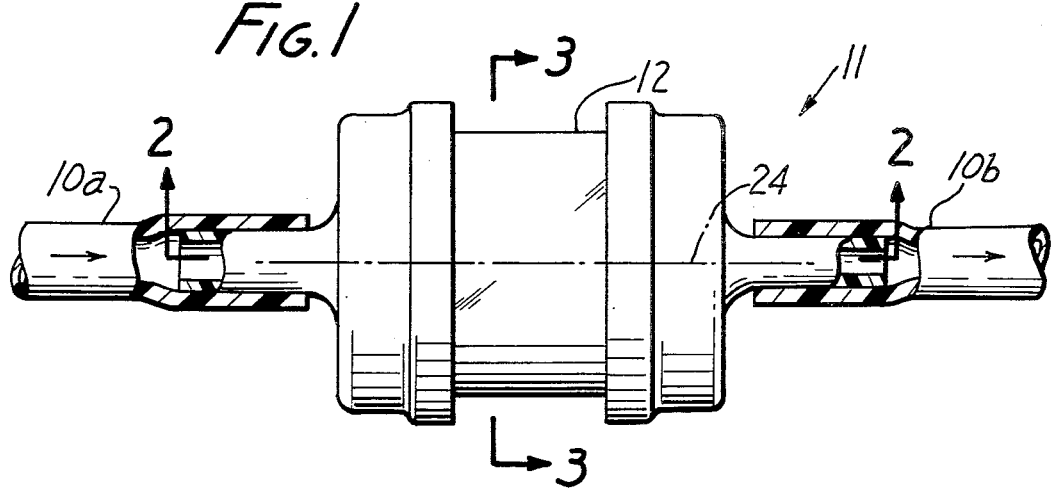
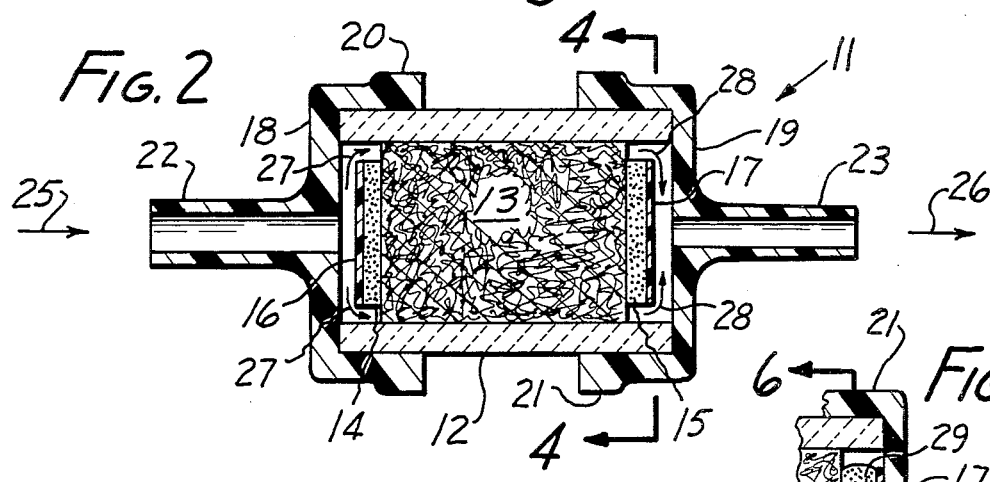
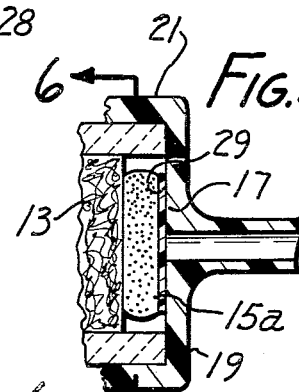
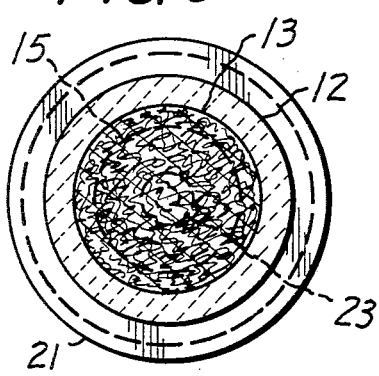 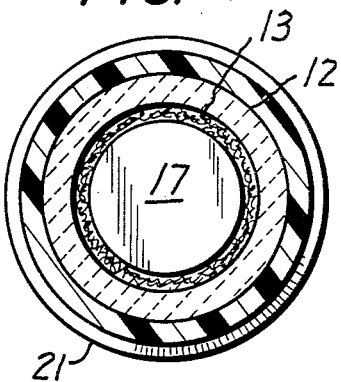 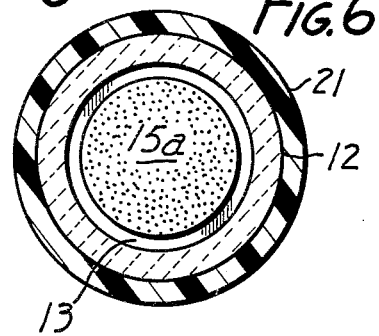

REFLUX CHECK VALVE

This invention relates to a reflux check valve and more particularly to such a valve which permits the transmission of dry gas through it while preventing the passage of liquid through it.

It is sometimes desired to transmit dry gas from a source to a delivery point while preventing the flow of any liquid. A typical example is in the use of a catheter for supplying a gas to the bladder of a person. The insufflation of the bladder by an inert gas is sometimes desirable for medical purposes and this is done by means of a pump or pressure device which sends the gas through the catheter. It is generally important to prevent the flow of urine from the bladder back to the pump, as the presence of urine can damage the pump and contaminate the system, thereby requiring a cleanup and sterilization procedure.

An object of this invention is to provide a check valve which will permit the passage of dry gas while preventing the passage of liquid.

The invention is carried out by the provision of a container having two ports, one of which will connect with the pump or pressure device, and the other with the delivery conduit or catheter section. A plug of cellular meterial of a character which permits the flow of gas through it is placed in the container between two ports. At one end of the plug juxataposed to a port, and preferably at both ends juxtaposed to the respective ports, there is placed a member dimensioned so that gas can pass around it for communication between the gas conduit and the cellular material. This member, or members, faced with a non-wetting membrane skin, has the character of undergoing rapid expansion when contacted by a liquid. Hence when liquid, for example urine, reaches it, the member expands sufficiently to block passage of the liquid, thus preventing the liquid from reaching the pump.

The foregoing and other features of the invention will be better understood from the following detailed description and the accompanying drawing of which:

FIG. 1 shows a reflux check valve according to this invention installed in a catheter;

FIG. 2 is a cross-section view of the valve of FIG. 1 taken at line 2—2 of FIG. 1;

FIG. 3 is a cross-section view taken at line 3—3 of FIG. 1;

FIG. 4 is a cross-section view taken at line 4—4 of FIG. 2;

FIG. 5 is a cross-section view showing part of the structure of FIG. 2 after absorption of liquid; and FIG. 6 is a cross-section view taken at line 6—6 of FIG. 5.

Referring to the drawing, FIG. 1 shows a portion of a catheter which has been separated into two sections 10a and 10b between which there is inserted a reflux check valve 11 according to this invention. The catheter is of a common type in the form of flexible tubing ordinarily of a plastic material and preferably transparent. The check valve 11 comprises a hollow cylindrical member 12, open at both ends, ordinarily of a plastic material and preferably transparent. There is placed within the cylinder 12 (sometimes called a chamber) a plug 13 of an open cell foam material ordinarily of plastic having a cylindrical exterior surface which makes a sliding fit within the cylinder 12. The cellular structure permits the ready flow of fluid, either gas or liquid, through it from one end to the other.

Circular disc-like members 14 and 15 are attached to the circular ends of plug 13 which may be done by suitable adhesive. The diameters of the disc members 14 and 15 are equal and somewhat less than the diameter of cylinder 13. The material of the members 14 and 15 is one which has the property of expanding when contacted by liquid. A suitable material is such as a cellulose, for example a nitro-cellulose. This can be in a cellular form and is compressed so that it retains its size and shape as illustrated in FIG. 2, while dry. Preferably the end faces of the disc members 14 and 15 are covered by a thin sheet 16 and 17 of a material which does not readily let liquid pass through it, such as for example, a membrane of silicone rubber. These coverings 16 and 17 can be attached to the respective discs 14 and 15 by adhesive.

The open ends of cylinder 12 are covered by end members 18 and 19 having respective flanges 20 and 21 which fit closely around the exterior of cylinder 12 to which they are attached by adhesive, for example. Each of the end members 18 and 19 is provided with a tubular nipple 22 and 23 extending away from the cylinder 12 along its longitudinal axis 24. These nipples are adapted to fit tightly within the catheter sections 10a and 10b as illustrated in FIG. 1.

It is seen that dry gas will readily flow through the check valve from one end to the other. Arrow 25, for example, indicates the passage of gas into nipple 22 and arrow 26 indicates its emergence from nipple 23. In passing through the valve the dry gas will spread around the circumference of disc 14 as indicated by arrows 27, through the open cell structure of foam material 13 and around the circumference of disc member 15 as shown by arrows 28 and out through nipple 23. If however liquid should enter the valve and come into contact with the material of disc members 14 or 15 it will cause the material of these members to expand immediately in a longitudinal direction so that it blocks the passage of the liquid through the valve. Thus, for example if liquid should enter in the direction opposite arrow 26 into nipple 23 to reach disc 15 this disc will expand in size longitudinally as shown at 15a in FIG. 5. The disc expands to the end wall 29 of end member 19. After this expansion the non-wetting membrane skin 17, being impervious to the passage of liquid through it, seals against wall 29 as seen in FIG. 5, thus substantially preventing the passage of liquid to the foam material 13. If, by chance, some liquid should escape past membrane skin 17 and disc member 15 before the latter member has expanded sufficiently to prevent it, it will cause a similar longitudinal expansion of the other disc member 14 and consequent sealing by membrane 16, upon the wetting of member 14. Thus two blocking members are provided against the passage of liquid into nipple 22.

When the device is used with a catheter which is to be inserted into a person's bladder, the section 10b of the catheter will be passed through the urethra to the bladder in a known manner.

When the bladder is to be insufflated with a gas, the gas pump will be connected to section 10a and the dry gas will be pumped into the bladder. If, however, urine should reflux in the opposite direction from the bladder, and contacts the disc member 15, it will expand disc 15 to block the refluxing as described above, and if the liquid should reach disc 14, it will also expand that disc as explained above. Thus, the liquid is prevented from reaching the pump.

It is usually preferable that the foam material 13 be of a white color so that if urine should pass the first disc 15, it can readily be seen in the foam.

Although the invention has been described with particular reference to its use with a catheter, it will be understood that it is useful also in other systems where it is desired to transmit dry gas while blocking the flow of liquid. It will be understood that the pressurizing device need not necessarily be an ordinary pump as some other source of pressure may be used instead, such as for example, a pressure vessel.

This invention is not to be limited by the embodiments shown in the drawings and described in the description, which are given by way of example and not of limitation, but only in accordance with the scope of the appended claims.

I claim:

1. A reflux check valve for use in a gas flow system comprising:
   a hollow container having a longitudinal axis, a peripheral side wall around said axis, and a pair of ports spaced apart from each other;
   a plug of porous material within said side wall through which fluid can flow while passing from port to port;
   a material expandable when contacted by liquid, positioned within the container so that liquid flow into the container through at least one of said ports contacts said expandable material, said expandable material being attached to an end of said plug and confronting one of said ports, in proximity thereto;
   said expandable material being dimensioned to have an area less than that of the plug end, such that dry flow may occur through said plug end, and when not contacted by liquid, gas may freely flow past said expandable material from one port to the other and through said plug, but when said expandable material is contacted by the liquid, it expands within a region of the container to block the flow of liquid from one port to the other;
   whereby dry gas passed into the container through one of the ports freely flows through the container and emerges from the other port, but liquid entering the container through one of the ports is prevented from exiting through the other port.

2. A valve according to claim 1 in which said container has an end wall through which one of said ports passes, and in which a membrane covers the face of the expandable material while leaving the edges of the expandable material exposed to be contacted by liquid when liquid is present, said membrane being juxtaposed to said end wall, whereby the expandable material expands longitudinally to move said membrane into sealing engagement with said one of said ports.

3. A valve according to claim 2 in which expandable material covered by a membrane is attached to both ends of the plug.

4. A reflux check valve for use in a gas flow system, comprising:
   a hollow container forming an internal chamber with a central axis, with two ports entering said chamber on said axis, their locations of entry being spaced apart from each other, the internal structure of said container being such as to enable fluid to flow from one port to the other unless otherwise prevented;
   a pair of bodies of dry, compressed expandable material supported in said chamber, each said body confronting a respective one of said ports, said bodies being dimensioned such that gas can flow past them while flowing from one port to the other port, the said expandable material expanding when contracted by a liquid;
   a closure comprising a membrane on each said body of expandable material confronting the respective one of said ports, said bodies of expandable material being so proportioned and arranged that, when only dry gas contacts them, they remain compressed and each closure is spaced from the port it confronts to permit gas to flow therethrough, but when a body is contacted by liquid it expands to move and press its respective closure against its respective port to close the same and prevent flow of liquid through the valve.

5. A valve according to claim 4 in which a plug of porous material is placed between said bodies to support them in said chamber.

* * * * *